United States Patent
Wang et al.

(10) Patent No.: US 6,885,764 B2
(45) Date of Patent: Apr. 26, 2005

(54) HIGH SPEED Z-SMOOTHING METHOD AND APPARATUS FOR CT IMAGING SYSTEM

(75) Inventors: Sharon X. Wang, Brookfield, WI (US); Piero U. Simoni, New Berlin, WI (US); Thomas Toth, Brookfield, WI (US); Stephen Metz, Greenfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 679 days.

(21) Appl. No.: 09/990,979

(22) Filed: Nov. 21, 2001

(65) Prior Publication Data

US 2003/0097063 A1 May 22, 2003

(51) Int. Cl.[7] ................................................. G06K 9/00
(52) U.S. Cl. ......................... 382/131; 382/173; 378/4; 250/370.09
(58) Field of Search ................... 382/128, 129, 382/130, 131, 132, 133, 134, 170, 171, 203, 224, 254, 264, 270, 282, 319, 154, 173, 267; 250/363.05, 390, 370.9, 390.02; 378/98.4, 19, 21, 23, 28, 25, 98, 15, 4; 700/143, 155, 97; 356/39

(56) References Cited

U.S. PATENT DOCUMENTS

| | | | | |
|---|---|---|---|---|
| 5,430,783 A | * | 7/1995 | Hu et al. | 378/15 |
| 5,907,593 A | * | 5/1999 | Hsieh et al. | 378/4 |
| 6,173,029 B1 | * | 1/2001 | Xie et al. | 378/4 |
| 6,253,115 B1 | * | 6/2001 | Martin et al. | 700/97 |
| 6,275,562 B1 | * | 8/2001 | He et al. | 378/19 |
| 6,295,331 B1 | * | 9/2001 | Hsieh | 378/19 |
| 6,301,325 B1 | * | 10/2001 | Besson et al. | 378/15 |

* cited by examiner

*Primary Examiner*—Bhavesh M. Mehta
*Assistant Examiner*—Seyed Azarian
(74) *Attorney, Agent, or Firm*—Quarles & Brady, LLP; Carl Horton (57) ABSTRACT

A method and apparatus for quickly rendering thick CT slice images wherein the data corresponding to an optimal number of slice images to be combined to generate a thick image and the data set required to generate the thick image are determined as a function of an optimal Z-smoothing factor and wherein Z-smoothing is implemented in software that performs quickly and is useable with any helical weighting algorithm and Z-smoothing function.

20 Claims, 8 Drawing Sheets

HIGH SPEED Z-SMOOTHING METHOD AND APPARATUS FOR CT IMAGING SYSTEM

STATEMENT REGARDING FEDERALLY SPONSORED RESEARCH

Not applicable.

CROSS-REFERENCE TO RELATED APPLICATIONS

Not applicable.

CROSS-REFERENCE TO RELATED APPLICATIONS

Not applicable.

BACKGROUND OF THE INVENTION

The present invention relates to multi-slice helical computerized tomography and more particularly to an algorithm, method and apparatus for using the same which reduces the data acquisition time and data processing time required to generate an image.

In computerized tomography (CT) X-ray photon rays are directed through a region of interest (ROI) in a patient toward a detector. Attenuated rays are detected by the detector, the amount of attenuation indicative of the make up (e.g. bone, flesh, air pocket, etc.) of the ROI through which the rays traversed. The attenuation data is then processed and back-projected according to a reconstruction algorithm to generate an image of the ROI's internal anatomy. Generally, the "back projection" is performed in software but, as the name implies, is akin to physically projecting rays from many different angles within an image plane through the image plane, the values of rays passing through the same image voxels being combined in some manner to have a combined effect on the voxel in the resulting image. Hereinafter the data corresponding to rays which are back projected will be referred to as back projection rays.

During data acquisition, if a patient moves, artifacts can occur in the resulting image which often render images useless or difficult to use for diagnostics purposes. For this and other reasons, as in other imaging techniques, the CT industry is constantly trying to identify ways to reduce the duration of acquisition periods without reducing the quality of acquired data.

In addition, because huge amounts of data are acquired during an acquisition period and the processing methods for image reconstruction from the gathered data are relatively complex, a huge number of calculations are required to process data and reconstruct an image. Because of the huge number of required calculations, the time required to process collected data and reconstruct an image is appreciable. For this reason the CT industry is also constantly searching for new processing methods and algorithms which can speed up the reconstruction process.

Various CT system features and procedures have been developed to increase data acquisition speed and to speed up the reconstruction process. Some of the more popular features and procedures including fan beam acquisition, simultaneous multiple slice acquisition, helical scanning and half-scanning. In fan beam acquisition the source is collimated into a thin fan beam which is directed at a detector on a side opposite a patient. In this manner, a complete fan beam projection data set is instantaneously generated for a beam angle defined by a central ray of the source fan beam. The source and detector are rotated about an image plane to collect data from all (e.g., typically 360 degrees) beam angles. Thereafter the collected data is used to reconstruct an image in the image plane. Thus, fan beam acquisition reduces acquisition period duration.

With respect to half-scanning, assuming a patient remains still during a data acquisition period, conjugate data acquisitions (i.e., data acquired along the same path from opposite directions) should be identical. In addition, using a fan beam, at least one ray can be directed through an image plane from every possible beam angle without having to perform a complete rotation about the patient. As known in the industry, data corresponding to every beam angle corresponding to a single imaging plane can be collected after a $(\pi+2\gamma)/2\pi$ rotation about the patient. Because less than an entire rotation about the imaging plane is required to acquire the imaging data these acquisition methods and systems are generally referred to as half-scan methods and systems. Thus, half-scan acquisition has been employed to reduce acquisition period duration in conjunction with single row detectors. In addition, because relatively less data has to be processed in the case of half-scan imaging methods and systems to generate an image, half-scan methods and systems also have the advantage of potentially reducing data processing and reconstruction times.

While fan beams and half-scans have several advantages, often, during a diagnostics session, a system operator will not know the precise location within a patient of an object, cavity, etc., of interest to be imaged. For this reason, it is advantageous for a system operator to be able to generate several cross sectional images in rapid succession by selecting different image/reconstruction planes. In these cases rapid data processing is extremely important to minimize delays between image generation so that a user does not lose her train of thought between image views.

Single slice detectors, fan beams and half-scans can be used to generate data in several different parallel image planes which, after data acquisition, can be used by a processor to generate an image anywhere between the image planes through interpolation/extrapolation procedures known in the art. While such systems work, unfortunately, the acquisition time required to generate data corresponding to many image planes is excessive and inevitable patient movement often causes image artifacts.

One way to speed up data acquisition corresponding to several image planes is by employing a multi-row detector with a fan beam. In multi-row detector systems, a relatively thick fan beam is collimated and directed at a multi-row detector with a patient there between, each detector row in effect gathering data for a separate "slice" of the thick fan beam along the Z or translation axis perpendicular to a fan beam width. Despite each detector row having a thickness, in these systems it is assumed that the detected signals in each row correspond to a plane centered within the row as projected onto the isocenter Z. Hereinafter the central plane through a row will be referred to as a row center.

After data acquisition an interface enables a system user to select an image plane from within the area corresponding to the collected data. The selected image plane is typically between the row centers of at least two adjacent detector rows. After image plane selection, a processor interpolates between data corresponding to adjacent rows to generate back projection rays corresponding to the selected image plane. When another image corresponding to a different image plane is desired, after selecting the plane, the processor again identifies an acquired data subset for interpolation, additional processing and back projection. Thus, multi-row detector systems further reduce data acquisition period duration where several image planes may be selected for reconstruction.

One limitation with multi-row detectors is that, during a single acquisition period, data can only be collected which corresponds to the detector thickness. To collect additional data corresponding to a ROI that is linger in the Z axis than the width of the detector, after one acquisition period corresponding to a first portion of the ROI, the patient has to be moved along the Z axis until a second portion of the ROI which is adjacent the first portion of the ROI is between the source and detector. Thereafter a second acquisition process has to be performed. Similarly, to collect additional data corresponding to a third portion of the ROI the patient has to be transported to another relative location with respect to the source and detector. Required translation without acquisition necessarily prolong the acquisition period and the additional acquisition time and aligning processes inevitably result in relative discomfort, additional patient movements and undesirable image artifacts.

Helical scanning systems have been developed so that data can be collected during a single acquisition period without halting patient translation during the acquisition period. In a helical scanning system, the source and detector array are mounted on opposing surfaces of an annular gantry and are rotated there around as a patient is transported at constant speed through the gantry. The X-ray beam sweeps a helical path through the ROI, hence the nomenclature "helical scanning system". Data acquisition can be sped up by increasing operating pitch (i.e., table translation speed relative to gantry rotation rate).

Various combinations of the fan-beam, multi-slice and half scan and helical scanning features have been combined to realize synergies and have been somewhat successful. By combining various of the speed enhancing features, data acquisition period durations are appreciably reduced thereby increasing system throughput and increasing image quality by minimizing the likelihood of patient movement.

While systems that combine several speed enhancing features are fast becoming a standard, not surprisingly, because of the complex data acquisition cycles that take place in such systems, the algorithms needed to combine subsets of acquired data into images have become extremely complex. To this end, exemplary helical weighting algorithms are described in an article entitled "Multi-Slice Helical CT: Scan and Reconstruction" by Hui Hu which was published in the January 1999 issue of Medical Physics, vol. 26, No. 1, pages 1 through 14. In operation, after imaging data has been collected and archived for a specific three dimensional ROI, an imaging system operator selects a specific slice and slice thickness through the ROI for image reconstruction and display. When a slice is selected, the processor applies a weighting and filtering function to the data to generate the intended image. The weighting function is dependent upon which slice is selected for reconstruction and viewing and on the pitch at which the data was collected. Therefore, each time a new slice is selected, a completely different weighting function which is pitch and slice dependent, has to be determined and applied to the acquired data and the weighted projection data has to be re-filtered again to generate a desired image.

While helical weighting function may take any of several different forms, an exemplary helical weighting function corresponding to a single slice image at a Z axis location Z1 typically includes a triangle having a value of one at a triangle apex Z1 location and tapering off to either side thereof down to zero.

Complicating matters, according to some diagnostic techniques it is advantageous to generate a two dimensional image corresponding to a "thick slice" through a ROI or a thick slice of interest (TSOI). For instance, in some cases it may be advantageous to generate a two dimensional image of a 10 mm thick volume through a ROI. Algorithms to generate a "thick image" have to combine data from several different two dimensional slice images through the TSOI. Early algorithms that used helical data to generate a thick image first generated a plurality of separate thin slice images through the TSOI using standard weighting, combining, filtering and back projection techniques and then combined the separate slice images using one of several different "Z-smoothing" functions that weight data from each image generally as a function of distance from a central imaging plane that bisected the TSOI.

In addition to being extremely slow, these early techniques were cumbersome and difficult to use as several imaging parameters had to be selected by a system operator that affected final image quality and often the only way to determine if optimal parameters had been selected was to generate and observe various characteristics of resulting images. For instance, some important parameters include image artifacts, noise, the well known slice sensitivity profile (SSP: i.e., response of the detector to a small homogeneous object as a function of the object position along the Z axis) and related full width at half maximum measurement (FWHM: i.e., full width of the SSP at half the maximum amplitude of the SSP), etc. Where the resulting image characteristics were unacceptable (e.g., excessive noise occurred, etc.), the operator had to alter the imaging parameters, regenerate images corresponding to the new parameters and then observe the images to determine if acceptable characteristics resulted.

One of the most important thick image imaging parameters is the number N of slice images (i.e., TSOI slice images) through the TSOI that are combine to generate the thick image. Ideally the number N should be as small as possible so that the processing time required to generate the thick image is minimized. However, if the number of slice images combined to generate a thick image is to small, the shape of the SSP becomes irregular making it very difficult to measure slice thickness or the FWHM. In addition, if the number of combined images is to small the resulting image may have some irregularities and may not actually provide a true representation of the anatomical structures within the TSOI.

Two other well known system parameters that are important in the case of thick image generation include a Z-smoothing factor zsf and an image weighting factor kw that are typically set during a commissioning process by iterative adjustment and as a function of resulting image characteristics. Several optimization schemes have been developed to optimize factors zsf and kw and any of those schemes may be employed in conjunction with the present invention. See for instance, U.S. Pat. No. 6,295,331 entitled "Methods And Apparatus For Noise Compensation In Imaging Systems" which issued on Sep. 25, 2001 and U.S. Pat. No. 6,173,029 entitled "Higher Order Detector Z-Slope Correction For A Multislice Computed Tomography System" which issued on Jan. 9, 2001, and which are assigned to the assignee of the present invention.

Recently algorithms have been developed that skip the intermediate processes associated with generating separate slice images through a TSOI and instead, after a TSOI has been selected by an operator, weight and combine helical data to directly generate a thick image corresponding to the TSOI. To this end, after factors zsf and kw have been optimally set, a TSOI has been selected and the number N of slice images through the TSOI to be combined has been selected, a processor identifies Z-smoothing weights for each slice image and combines the Z-smoothing weights and helical weights for each image to generate a thick image weighting function corresponding to an entire helical data sub-set that is subsequently used to generate the thick image.

Because a typical slice image helical weighting function extends along the Z-axis and often the number of TSOI slice images to be combine to generate a thick image requires spatially close slice images, often the helical weighting functions corresponding to adjacent TSOI slice images overlap. Overlapping weighting functions along with hardware constraints have caused, prior processes of combining helical slice weighting functions to be relatively computationally complex requiring various reading, adding and writing steps.

To this end, exemplary hardware employed to apply z-smoothing weights and combine overlapping helical weighting functions to generate a thick image weighting function includes a processor having first and second blocks of internal memory where first and second functions to be added together have to be stored in the separate first and second blocks, respectively.

With the limited hardware architecture described above, assume that each two adjacent weighting functions corresponding to four adjacent slice images overlap along a range of gantry angles. In this case, prior algorithms to apply z-smoothing weights to each of the first and second functions and then add the functions together included applying the z-smoothing weight to the first helical weighting function and storing the resultant in the second block and then applying the z-smoothing weight to the second helical weighting function and storing the resultant in the first block. Thereafter, to add the first two helical weighting functions together included, for each gantry angle β corresponding to either the first or second helical weighting function, reading a first weight corresponding to the first weighting function from the second block, reading a second weight corresponding to the second weighting function from the first block, adding the first and second weights together and then writing the summed weight to a final weighting array. The final array is stored within the first block. This four step process had to be repeated for every gantry angle β corresponding to at least one of the first and second weighting functions.

Thereafter, to apply a z-smoothing weight to the third helical weighting function and add the resultant to the final (i.e., summed) weighting function a z-smoothing weight corresponding to the third image was applied to the function in the first block and the resultant was restored in the first block. Thereafter, for each gantry angle corresponding to either the original second weighting function or the third weighting function, the algorithm included reading a first weight corresponding to the final weighting function, reading a second weight corresponding to the third weighting function from the first block, adding the first and second weights together and then writing the summed weight to a final weighting array. Once again. this four step process had to be repeated for every gantry angle corresponding to at least one of the second and third weighting functions. A similar process had to be performed to apply z-smoothing weight to the fourth helical weighting function and add the resultant to the final weighting function.

While four process cycles may not, at first blush, appear to be extremely burdensome, when there are a massive number of such combinations, the combined periods have been known to cause delays as long as several seconds between thick slice selection and image presentation. While several seconds may not seem extremely time consuming where only a single thick slice image is required, often system operators prefer to select different thick images for display in rapid succession so that various portions of the ROI can be observed during an imaging session. In these cases even a few seconds can seem like an eternity to a system operator attempting to quickly cycle through images to identify a specific anatomical phenomenon.

Thus, it would be advantageous to have a system that could help a system operator optimize various system parameters associated with thick image processing thereby reducing the number of iterations required to generate an acceptable image and reducing uncertainty regarding whether or not a final image is the best possible image and that could speed up the processing time required to generate a thick image after a TSOI has been selected.

SUMMARY OF THE INVENTION

It has been recognized that the process performed by a reconstructor processor for combining a helical weighting algorithm and detector row specific Z-smoothing weights (i.e., scalars) can be streamlined to reduce the processing time and hence the time between TSOI selection and presentation of a corresponding image. More specifically, it has been recognized that often when two weighting functions are being added, only a sub-range of gantry angles between the two weighting functions overlap and therefore it is not necessary to perform the addition step of the process for the gantry angles that do not overlap. By simply eliminating the addition steps when not required, processing time is reduced appreciably.

Moreover, it has been recognized that after certain operating parameters have been optimally set during a commissioning procedure, other parameters may automatically be identified by a processor thereby reducing the guess work associated with complete optimization. More specifically, after optimal z-smoothing factor zsf has been set using any of several known algorithms, the optimal number of slice images that should be combined to generate a thick image may be determined as a function of the z-smoothing factor zsf.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE DRAWINGS

FIG. 14a is a schematic diagram illustrating a helical data subset corresponding to a gantry scan range for the center detector in a detector row during a half scan required to generate a single thin slice image while

DESCRIPTION OF THE PREFERRED EMBODIMENTS

A. Hardware

Figure 1:
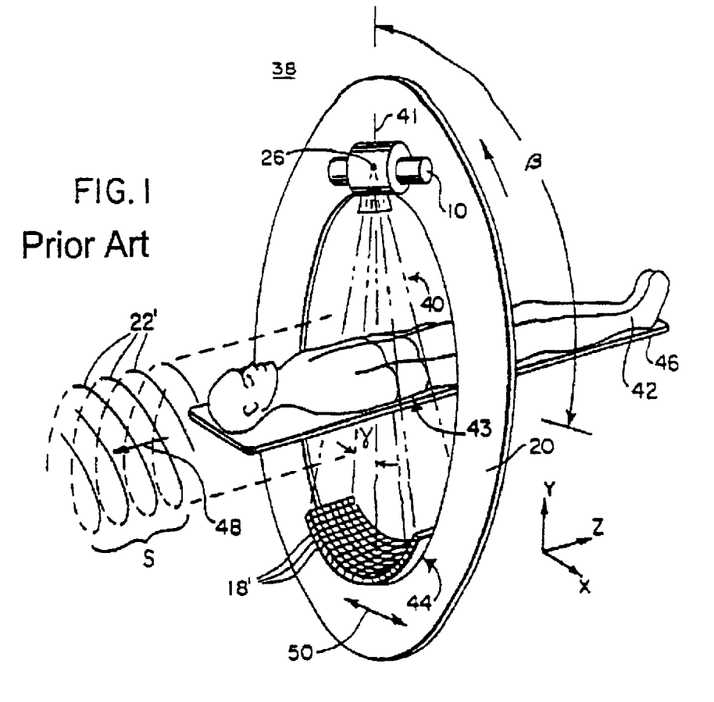
FIG. 1 is a perspective view of a CT apparatus used to practice the present invention which includes a detector array having rows and columns of detector elements and fan beam source.

Referring now to FIG. 1, a CT scanner for use with the present invention includes a gantry 20 having an opening (i.e., defining an imaging area) supporting an x-ray source 10 oriented to project a fan beam 40 of x-rays along the beam axis 41 through a patient 42 to a supported and opposed detector array 44. The gantry 20 rotates to swing the beam axis within a gantry plane 38 defining the x-y plane of a Cartesian coordinate system. Rotation of the gantry 20 is measured by beam angle $\beta$ from an arbitrary reference position within the gantry plane 38.

A patient 42 rests on a table 46 which may be moved along a translation axis 48 aligned with the Z-axis of the Cartesian coordinate system. Table 46 crosses gantry plane 38 and is radio-translucent so as not to interfere with the imaging process.

Figure 3:
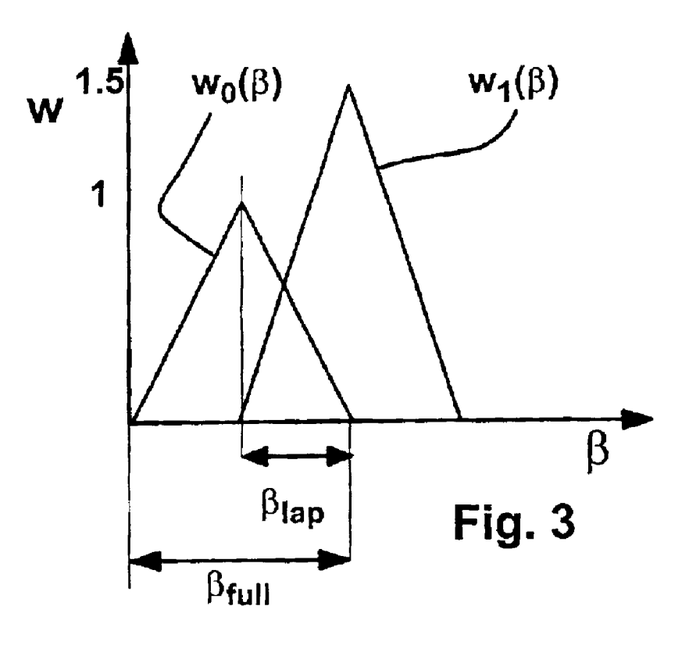
FIG. 3 is a graph illustrating two exemplary helical weighting functions and an exemplary overlapping range $\beta_{lap}$ corresponding to the two functions.

The x-rays of the fan beam 40 diverge from the beam axis 41 within the gantry plane 38 across a transverse axis 50 generally orthogonal to both the beam axis 41 and the translation axis 48 at a fan beam angle $\gamma$. The x-rays of beam 40 also diverge slightly from the beam axis 41 and the gantry plane 38 across the translation axis 48. Referring also to FIG. 3, a maximum beam angle $\gamma$ is identified by symbol $\Gamma$.

After passing through patient 42, the x-rays of the fan beam 40 are received by detector array 44 which has multiple columns of detector elements 18'. The detector elements 18' in exemplary array 44 are arranged in eight rows (i.e., array 44 is an eight slice detector) extending along the traverse axis 50 that subdivide array 44 along the Z-axis and a plurality of columns extending along Z or translation axis 48. The width of detector array 44 is measured along Z-axis 48. The surface of detector array 44 may be planar or may follow a section of a sphere or cylinder having a center at focal spot 26 or alternatively at the system isocenter.

The detector elements 18' each receive x-rays and provide intensity measurements along separate rays of the fan beam 40. Each intensity measurement describes the attenuation via a line integral of one fan beam ray passing through a portion of volume 43 of patient 42. The dimension of volume 43 along Z-axis 48 is greater than the Z-axis width of eight slice array 44.

Figure 2:
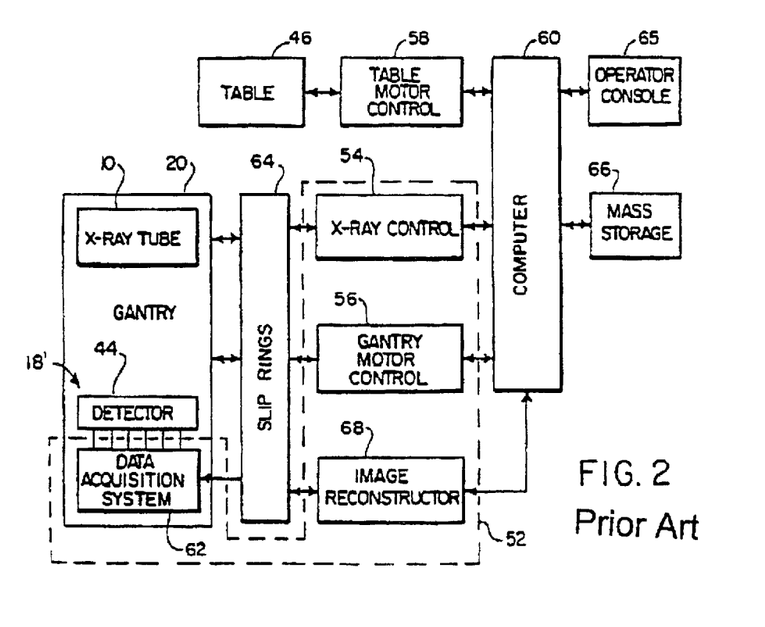
FIG. 2 is a block diagram of CT control system which may be used to control the CT apparatus of FIG. 1 and which is useful for the purposes of practicing the present invention.

Referring to FIGS. 1 and. 2, an exemplary control system for controlling the CT imaging system of FIG. 1 includes gantry associated control modules collectively identified by numeral 52, a table motor control 58, slip rings 64, a central processing computer 60, an operator's console 65 and a mass storage device 66. Modules 52 include an x-ray control 54, a gantry motor control 56, a data acquisition system 62 and an image reconstructor 68. X-ray control 54 provides power and timing signals to the x-ray source 10 to turn it on and off as required under the control of a computer 60. Gantry motor control 56 controls the rotational speed and position of the gantry 20 and provides information to computer 60 regarding gantry position. Data acquisition system 62 samples and digitizes intensity signals from the detector elements 18' of detector array 44 provides the digitized signals in the form of helical data row views to computer 60 for storage in mass storage device 66. Reconstructor 68 is linked to computer 60 for receiving slice image data there from and back projects the received data to, as its label implies, construct a slice image for viewing or that can be manipulated in some other manner.

Each of the above modules is connected to associated gantry mounted components via slip rings 64 and is also linked to computer 60 for control purposes Slip rings 64 permit gantry 20 to rotate continuously through angles greater than 360° to acquire projection data.

The speed and position of table 46 along translation axis 48 is controlled by computer 60 by means of table motor control 58. In addition, computer 60 runs a pulse sequencing program to perform the inventive data processing method as described in more detail below. Computer 60 receives commands and scanning parameters via operator console 65 that generally includes some type of visual interface device (e.g., a CRT display) and one or more input devices (e.g., a keyboard, a mouse controlled display cursor, etc.). Console 65 allows an operator to enter parameters for controlling a data acquiring scan and to display constructed image and other information from computer 60.

Mass storage device or memory 66 provides a means for storing operating programs for the CT imaging system, as well as image data for future reference by the operator. Both computer 60 and the image reconstructor 68 have associated electronic memory (not shown) for storing data and pulse sequencing programs.

In operation, gantry motor control 56 brings gantry 20 up to a rotational speed and table motor control 58 begins translation of table 46 along translation axis 48. The x-ray control 54 turns on x-ray source 10 and projection data is acquired on a continuous basis. The table 46 translation speed relative to the gantry rotation rate is referred to as the operating "pitch" p. At each beam angle $\beta$, the projection data acquired comprises intensity signals corresponding to each detector element 18' at each particular column and row of array 44. The collected data is stored in storage device 66 as helical data including row views correlated by gantry angle β.

Figure 12:
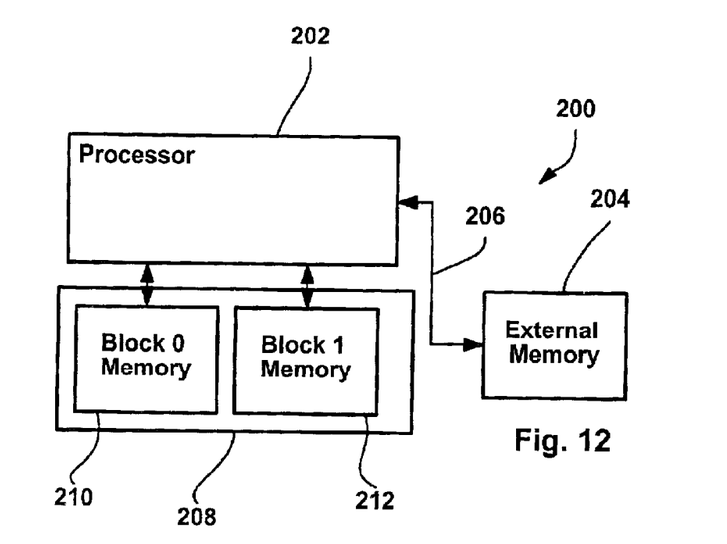
FIG. 12 is a schematic diagram illustrating a processor and other hardware employed to carry out the summing methods of the present invention.

Referring to FIG. 12, a typical hardware platform 200 employed to carry out the process of combining z-smoothing scalars and helical weight functions is illustrated and includes a processor 202 and an external memory 204 that are linked via a data bus 206. Processor 202 includes a small amount of internal memory 208 including first and second memory blocks 210 and 212, respectively. Generally, during operation, processor 202 moves a helical weighting function from external memory 204 to internal memory block 210 (i.e., block 0) and z-smoothing scalars zw(n) are stored as a small array in block 212. The helical weighting function is a function that is generally applicable to each image to be combined to generate a thick image while the z-smoothing scalars zw(n) are image specific. Importantly, block 210 is a relatively small memory bank which can only store a data array having a size similar to that of the helical weighting function (e.g., approximately 1000 weight values corresponding to different gantry angles β). Processor 202 manipulates the stored weights in a manner described in more detail below to generate a thick image weighting function $w_{ti}(β)$.

B. Theory

Figure 14A:
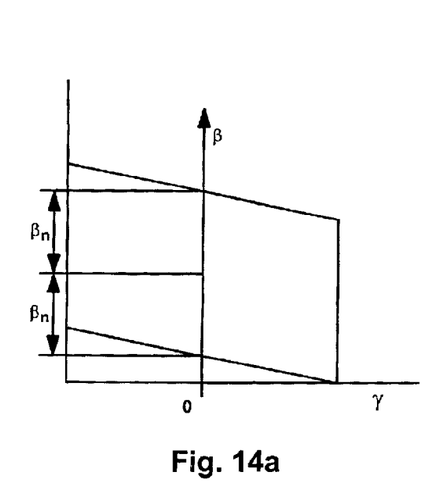
Figure 14B:
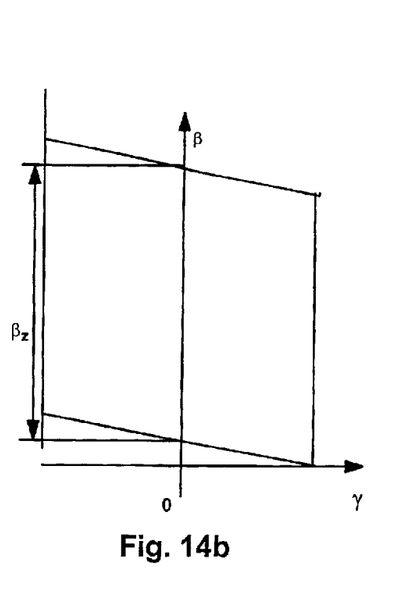
FIG. 14b is a schematic diagram illustrating a data subset corresponding to a gantry scan range for the center detector in a detector during a scan required to generate a thick image using a z-smoothing function.

A z-smoothing factor zsf can be optimized during a commissioning process using any of several different optimization processes well known in the art. It has been recognized that an optimal z-smoothing factor zsf can also be expressed as an equation that relates the factor zsf to gantry rotation required to generate a single thin slice image and gantry rotation required to generate a thick image of a TSOI using a z-smoothing mode of operation. More specifically, factor zsf can be expressed as $$zsf = \frac{β_z}{β_n} - 1 \qquad \text{Eq. 1}$$

where, referring to FIGS. 14a and 14b, $β_n$ corresponds to half of the maximum gantry rotation angle range spanned by a center detector in any detector row during data acquisition required to generate a thin slice image and $β_z$ corresponds to the maximum gantry rotation angle range spanned by the center detector of the same row during data acquisition required to generate a thick slice image via z-smoothing. Equation 1 can be rewritten to solve for range $β_z$ as:

$$β_z=(zsf+1)β_n \qquad \text{Eq. 2}$$

Angle range $β_n$ can be expressed as $$β_n = k\frac{2π}{p} \qquad \text{Eq. 3}$$

where k is a function of a z-smoothing algorithm (having a range between 0 and 1) and is set once the z-smoothing algorithm is selected while p is the system pitch used during data acquisition. Both factor k and pitch p are set and therefore known. Thus, where factor zsf can be determined through an optimization process, Equations 2 and 3 can be solved to identify the precise range $β_z$ over which data must be weighted and combined to generate a thick image.

Moreover after factor zsf has been determined, it has been recognized that an optimal number zsn of images to be combined in the z-smoothing mode to generate an image of a TSOI may be determined by solving the following equation:

$$zsn=2f_{ceil}(zsf-1)+1 \qquad \text{Eq. 4}$$

where $f_{ceil}$ is a function that increases a decimal value in the parentheses to the next highest integer (e.g., 1.1 becomes 2, etc.). Function $f_{ceil}$ generally ensures that the optimal number zsn is odd.

Note that herein number zsn is referred to as the "optimal number" of images to be combined to generate a thick image. Nevertheless, according to the present invention zsn images are never generated. Instead, number zsn is used to manipulate weighting functions thereby generating a thick image weighting function $w_{ti}(β)$ to be applied to data range $β_z$ thereby skipping the step of generating zsn images but achieving an identical result.

In addition to optimizing the z-smoothing factor zsf during commissioning, a k weight factor kw is also typically adjusted for optimization via any of several different optimization processes known in the art. Thereafter, any of several different z-smoothing functions can be used to identify a separate z-smoothing scalar zw(n) to be applied to each of the zsn images. One exemplary linear z-smoothing weighting function can be expressed as:

$$zw(n)=zw(zsn-1-n)=kw+2n(1-kw)/zsn-1 \qquad \text{Eq. 5}$$

where 0<n≤(zsn+1)/2.

Referring now to FIG. 3, two z-scaled helical weighting functions $w_0(β)$ and $w_1(β)$ are illustrated that correspond to first and second adjacent image. For the purposes of this explanation a full function scan angle range will be identified as $β_{full}$. For example, in FIG. 3, full range $β_{full}$ corresponding to function $w_0(β)$ is identified. Although not separately identified, function $w_1(β)$ is also characterized by a full range $β_{full}$. An overlapping range $β_{lap}$ is common to each function $w_0(β)$ and $w_1(β)$.

Herein, to simplify this explanation, to identify a specific range of any function, a range identifying convention will be adopted wherein the range will be referenced by two values in parentheses and separated by a comma. The first value identifies the beginning of the range within a corresponding weighting function and the second value identifies the range length in scan angle β. For instance, the overlapping range corresponding to function $w_0(β)$ in FIG. 3 will be specified as $w_0(β_{full}-β_{lap}, β_{lap})$ where $β_{full}-β_{lap}$ is the beginning of the range within function $w_0(β)$ and $β_{lap}$ is the length of the range. Similarly, the overlapping range corresponding to function $w_1(β)$ in FIG. 3 is specified as $w_1(0,β_{lap})$ where 0 is the beginning of the range with respect to the specific function $w_1(β)$ and $β_{lap}$ is the range length and the non-overlapping range corresponding to function $w_1(β)$ is specified as $w_1(β_{lap}, β_{full}-β_{lap})$ where $β_{lap}$ is the beginning of the range within function $w_1(β)$ and $β_{full}-β_{lap}$ is the length of the range.

Using the convention of specifying ranges described above, an example of how weights are combined according to the present invention is helpful to understanding the present invention. To this end, the present example will illustrate how functions $w_0(β)$ and $w_1(β)$ in FIG. 3 are combined according to the inventive process. In FIG. 3 and the following figures, function $w_0(β)$ and $w_1(β)$ are shown after scaling by z-smoothing scalars zw(n) has already been performed. In the example that follows, however, scaling is included as part of the process in order to be complete.

Referring now to FIGS. 4a through 10b, a series of graphs illustrate a scaling and function combining process consistent with the present invention. While observing the graphs in FIGS. 4a–10b, it should be recognized that the "a" series graphs (e.g., FIGS. 4a, 5a, 6a, etc.) are only indicative of the process performed by the z-smoothing processor and are not meant to be literal interpretations. For instance, the graph in FIG. 5a indicates that data corresponding to a complete function $w_1(\beta)$ is accessed by the processor at a specific instant in time when, in reality, only one of the weight values corresponding to the illustrated function $w_1(\beta)$ is accessed during a processor cycle. Similarly, the series "b" graphs (e.g., FIGS. 4b, 8b, etc.) illustrate the content of an intermediate memory (e.g., 212 in FIG. 12) after specific processing intervals and is constructed on a point by point basis as weights are added by processor 202.

Figure 4A:
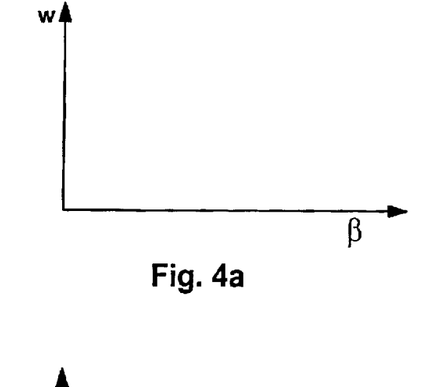
FIG. 4a is a schematic illustrating processor data manipulation at one instant during a weight summation process and FIG. 4b is a graph corresponding to the graph of FIG. 4a, albeit illustrating the content of an intermediate thick image weighting function array $w_{int}(\beta)$ at one instant during a weight summation process.
Figures 8A, 8B:
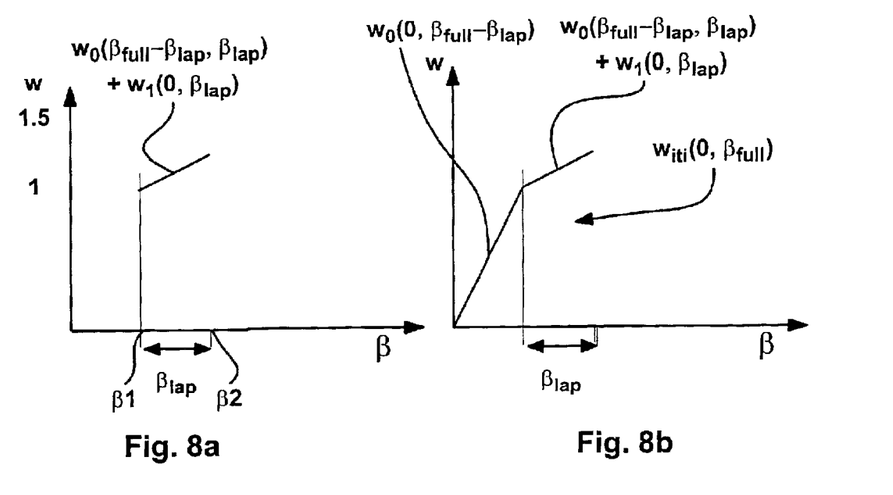
FIGS. 8a and 8b are similar to FIGS. 4a and 4b, albeit illustrating another instant during a summation process.

Referring still to FIGS. 4a and 8b, each graph corresponding to the "a" series illustrates data accessed by processor 202 during a process corresponding to combining weights from functions $w_0(\beta)$ and $w_1(\beta)$. The "b" series graphs illustrate an intermediate thick image weighting function $w_{iti}(\beta)$ at different stages of the combining process illustrated in associated "a" series graphs. Where there is no b series graph corresponding to an a series graph, the b series intermediate weighting function remains unchanged from the previous b series graph.

Figure 4B:
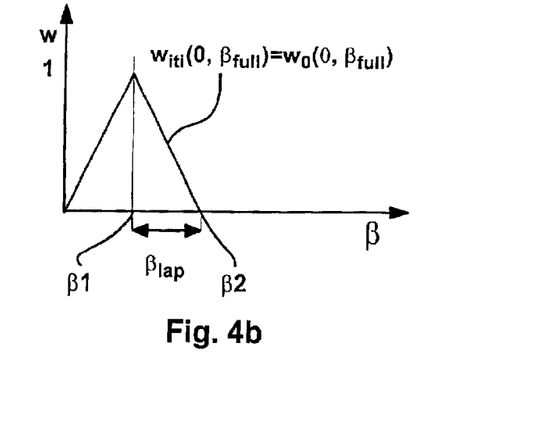
Figure 5A:
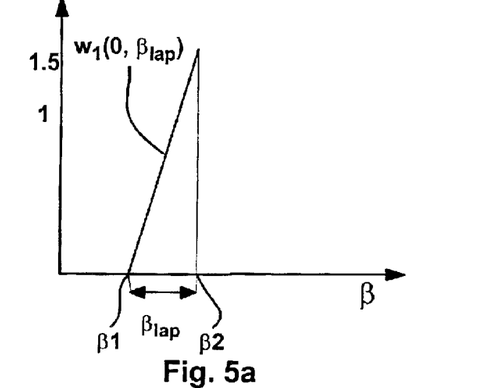
FIG. 5a is similar to FIG. 4a, albeit illustrating another instant during a summation process.
Figure 6A:
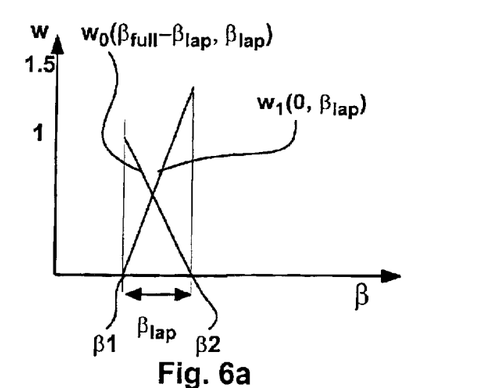
FIG. 6a is similar to FIG. 4a, albeit illustrating another instant during a summation process.

Referring specifically to FIGS. 4a and 4b and also to FIG. 12, initially, it is assumed a z-smoothing scalar has been applied to function $w_0(\beta)$ and the resultant function $w_0(\beta)$ is stored as intermediate thick image function $w_{iti}(\beta)$ in an intermediate array in memory block 212 and that the processor memory is blank. Helical weighting function $w_1(\beta)$ (see also FIG. 3) to which a z-smoothing weight has already been applied and to be combined with the intermediate function $w_{iti}(\beta)$ is stored in block 210. Referring to FIG. 5a, during a first processor cycle, processor 202 reads a first value of weighting function $w_1(\beta)$ from memory 210. For instance, in FIG. 5a, the first value corresponds to angle $\beta 1$. Referring also to FIG. 6a, during a second processor cycle processor 202 reads a first value of intermediate thick image function $w_{iti}(\beta)$ that corresponds to angle $\beta 1$.

Figure 7A:
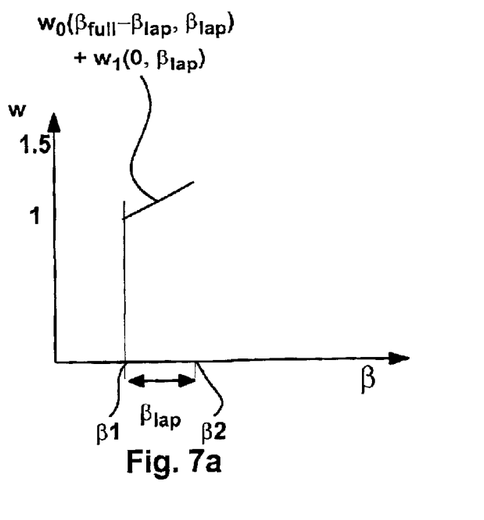
FIG. 7a is similar to FIG. 4a, albeit illustrating another instant during a summation process.

Referring to FIG. 7a, during a third processor cycle, processor 202 adds the weight values from each of functions $w_1(\beta)$ and $w_{iti}(\beta)$ at angle $\beta 1$ to generate an added weight value at angle $\beta 1$. Referring to FIG. 8b, processor 202 stores the summed value to intermediate thick image function $w_{iti}(\beta)$ at angle $\beta 1$. Thus, the process described above requires four processor cycles to combine two weight values including reading, reading, adding and storing cycles corresponding to FIGS. 5a, 6a, 7a and 8b, respectively. This four step process is repeated for each $\beta$ value in the overlapping range $\beta_{lap}$ (see FIG. 3). In an exemplary system, there may be nearly 1000 $\beta$ values in the $\beta_{full}$ range so that the four step process often must be performed several hundreds of times for each overlapping range $\beta_{lap}$ (e.g., for the range Plap between $\beta 1$ and $\beta 2$ in FIG. 6a the process may be performed several hundreds of times).

Figure 9A:
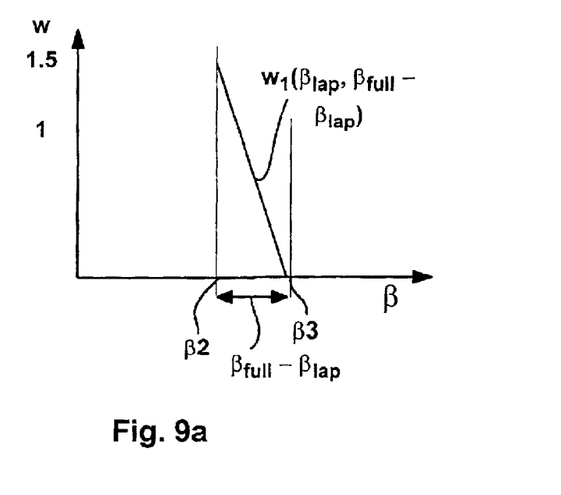
FIG. 9a is similar to FIG. 4a, albeit illustrating another instant during a summation process.
Figures 10A, 10B:
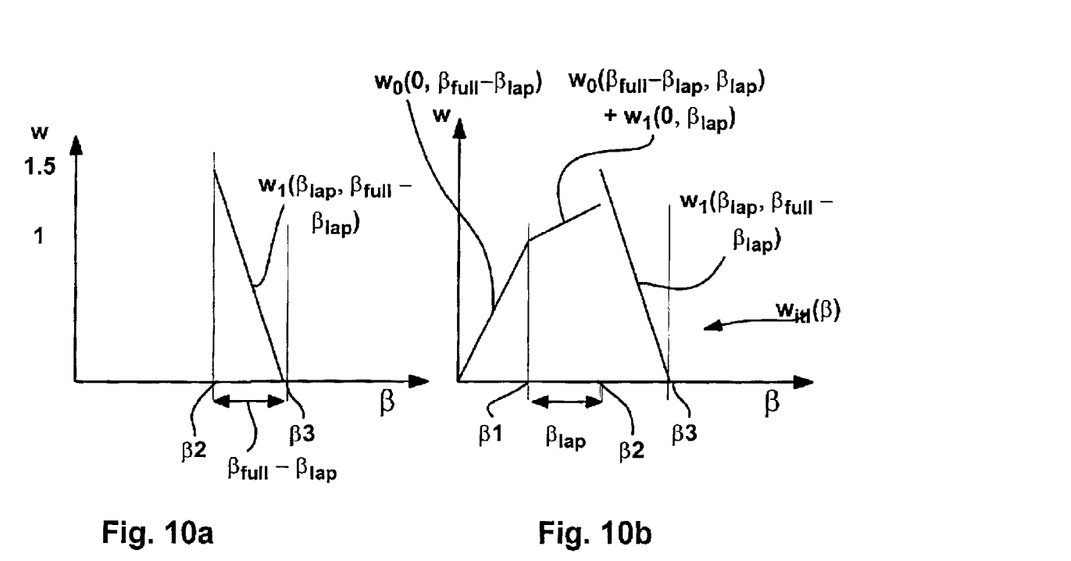
FIGS. 10a and 10b are similar to FIGS. 4a and 4b, albeit illustrating another instant during a summation process.

Referring now to FIG. 9a, after the overlapping range $\beta_{lap}$ weighting values have been added and stored, processor 202 next transfers the non-overlapping weight values corresponding to function $w_1(\beta)$ from memory block 210 to block 212 and maintains the correlation between weight values and angle values. This transfer process requires two processor cycles for each weight value transferred. Thus, as illustrated in FIG. 9a, each weight is first read from block 210 and as illustrated in FIG. 10b, each weight is then stored or written to block 212 so that the weight and $\beta$ angles are correlated. Once again the weight values are read and stored one at a time so that this two step process is performed several hundreds of time between angles $\beta 2$ and $\beta 3$.

Referring still to FIGS. 4a through 10b, the graph segments illustrated are labeled in a manner consistent with the labeling convention described above (i.e., a first value in parentheses identifies the beginning angle of a segment with respect to a corresponding weight and the second value indicates the length, in $\beta$, of the segment). Thus, for instance, in FIG. 5a, the illustrated segment $w_1(0,\beta_{lap})$ includes the segment of function $w_1(\beta)$ starting at the beginning of the function (i.e., at angle 0) and has a length of $\beta_{lap}$. FIG. 7a illustrates that segment $w_1(0,\beta_{lap})$ values are added to segment $w_{iti}(\beta_{full}-\beta_{lap}, \beta_{lap})$ values and FIG. 8b indicates that the added segments are then stored to complete a summation process. Thereafter, FIG. 9a indicates that segment $w_1(\beta_{lap}, \beta_{full}-\beta_{lap})$ values are read by processor 202 and FIG. 10b indicates that the segment values are then stored to complete the transfer process.

The process described above is repeated for additional images until weighting functions corresponding to all zsn images (i.e., the optimal number of images) have been combined to generate a complete thick image weighting function $w_{ti}(\beta)$ and then the function is applied to imaging data corresponding to optimal range $\beta_z$, the weighted data is filtered and then back projected to generate the requested thick image.

C. Operation

Figure 11:
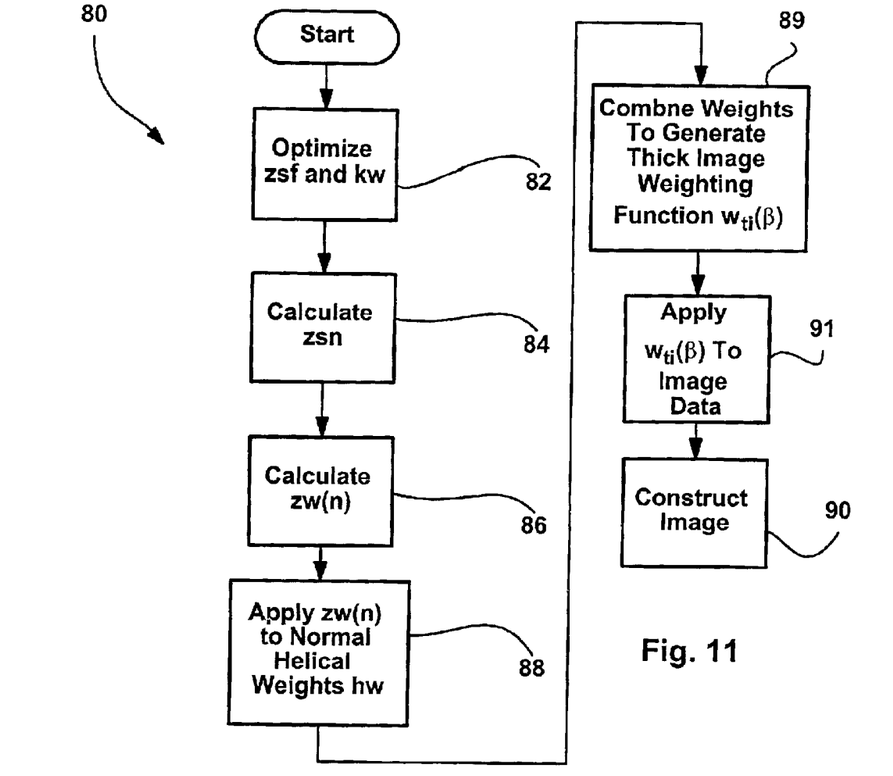
FIG. 11 is a flow chart illustrating a general z-smoothing method.

In operation, referring now to FIG. 11, a general z-smoothing process 80 is illustrated. At block 82, any of several well known optimization commissioning procedures are used to identify the z-smoothing factor zsf and the k-weighting factor kw. Thereafter, at block 84, the optimal number of images to be combined to generate a thick slice image is identified by solving Equation 4. Continuing, at block 86, the k-weight value kw and the optimal number zsn of images to be combined are plugged into a z-smoothing weighting function. For example, the values may be plugged into Equation 5 to generate the z-smoothing scaling factors zw(n), one scalar for each of the zsn images.

At block 88 the z-smoothing scalars zw(n) are applied to normal helical weights hw thereby generating scaled helical weight functions. Continuing, at block 89, the weights corresponding to overlapping weighting functions are combined to generate the thick image weighting function $w_{ti}(\beta)$ and at block 91 the thick image weighting function $w_{ti}(\beta)$ is applied to the image data.

Importantly, memory limitations make it necessary that process steps 88 and 89 be performed in a cyclic fashion. To this end, referring again to FIG. 12, memory blocks 210 and 212 have limited sizes and therefore cannot accommodate all z-smooth scaled helical weighting functions and a final thick image weighting function $w_{ti}(\beta)$ and the same time. For example, block 210, which stores the helical weighting functions, is only large enough to store a single weighting function at a time (i.e., block 210 can only store an array including less than 1000 weight values at a time and the helical function, at least in one exemplary system, includes 888 weight values). Thus, the scaling and summation processes are interleaved so that only one scaled weight function is stored in block 210 at a time and only two weight functions, the scaled function in block 210 and a portion of the intermediate thick image function in block 212, are combined at one time and the resulting function is stored as an updated intermediate function $w_{iti}(\beta)$. Therefore, the scaled weighting function in block 210 is rescaled to reflect a z-smoothing scalar associated with the next image to be combined with the updated intermediate function $w_{iti}(\beta)$ and the newly scaled function in block 210 is again summed with the intermediate function $w_{iti}(\beta)$ to re-update function $w_{iti}(\beta)$.

To perform the scaling process described above, after z-smoothing scalars zw(n) for each image to be combined to generate the thick slice have been identified, the scalars zw(n) are modified so that each can be used to rescale as a function of previous scalars that, during the scaling process, will alter the scaled weighting function stored in block 210. For instance, assume that a z-smoothing function is used to determine that an initial helical weighting function must be scaled two times, four times and six times for each of first, second and third images to be combined to generate a thick image, respectively. In this case, the scalars 2, 4 and 6 are replaced with scalars 2, 2 and 1.5, respectively. Thereafter, upon the first scaling, the resulting scaled function in block 210 is two times the initial weight values. The second scaling scales the function in block 210 (i.e., the weights that are already scaled by a factor 2) by another factor two thereby storing a function in block 210 that is four times the initial weight values. The third scaling scales the function in block 210 (i.e., the weights that are already scaled by a factor of 4) by a factor of 1.5 thereby storing a function in block 210 that is six times the initial weight values. Thus, proper z-smooth scaling can be accomplished without having to maintain the initial helical weight function in block 210 every time a new scaling is required.

Figure 13:
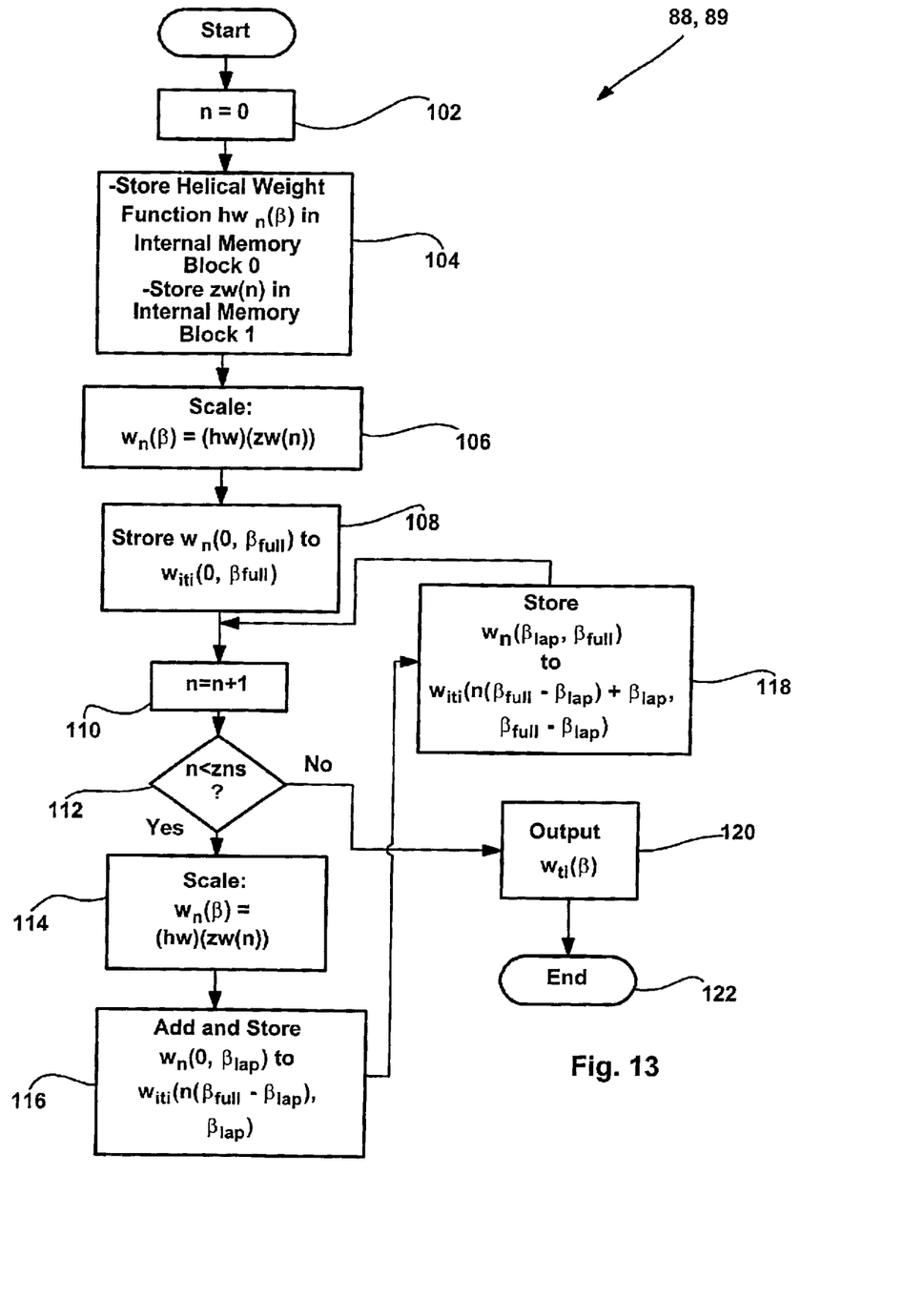
FIG. 13 is a flow chart illustrating a portion of the flow chart in FIG. 11 in greater detail.

Referring to FIGS. 11 and 13, process steps 88 and 89 are illustrated in more detail in FIG. 13. To this end, referring also to FIG. 12, after the z-smoothing scalars zw(n) have been calculated at block 86, control passes to block 102 where a counter n is set equal to zero. Next, at block 104, processor 202 moves the initial helical weighting function $hw_n(\beta)$ into the first internal memory block 210. In addition, at block 104, processor 202 moves the z-smoothing scalars zw(n) into second memory block 1.

At block 106, processor 202 retrieves the helical weighting function $hw_n(\beta)$ weighting values one at a time from within memory block 210 and scales each one of the values separately by multiplying the value by the corresponding z-smoothing scalar zw(n) and then stores each one of the scaled weighting values back in block 210 at the location from which the corresponding initial value was retrieved. After all of the weighting values corresponding to the function in block 210 have been scaled, control passes to block 108. At block 108, processor 202 moves the scaled weighting function from block 210 into the intermediate memory buffer earmarked for the intermediate thick image weighting function $w_{int}(\beta)$ in block 211. To this end, at block 108, processor 202 stores the entire weighting segment $w_n(0, \beta_{full})$ to the intermediate function $w_{int}(\beta)$ locations corresponding to $w_{int}(0, \beta_{full})$.

At block 110, counter n is incremented by one and control passes to block 112. At block 112, counter n is compared to the optimal number of images zns and, where counter n is equal to optimal number zns, control passes to block 120 where a final thick image weighting function $w_{ti}(\beta)$ is output after which the combining process ends at block 122. However, where counter n is less than optimal number zns, control passes to block 114 where the weighting function in block 210 is again scaled by a corresponding z-smoothing scalar associated with a next image to be combined to generate the thick image. In the present example, because counter n is one at this juncture, processor 202 accesses the scaling factor corresponding to the second image to be combined and uses that scalar to scale the weighting function. Once again, as in the case of block 106, the scaled weighting function is stored back into memory block 210 thereby over-writing the previously scaled function.

Continuing, at block 116, processor 202 adds the overlapping portions of the intermediate function $w_{int}(\beta)$ and the scaled second weighting function (i.e., the function stored in block 210) and stores the results in the intermediate function $w_{int}(\beta)$. To this end, referring once again to FIGS. 5a through 8b, the four step process described above is performed for each β value within the overlapping range $\beta_{lap}$. The adding and storing process in block 116 is represented by the relationship $w_n(0, \beta_{lap})$ to $w_{int}(n(\beta_{full}-\beta_{lap}), n(\beta_{full}-\beta_{lap})+\beta_{lap}))$. Next, at block 118, processor 202 stores the non-overlapping portion of the second scaled weighting function in a corresponding range of the intermediate function $w_{int}(\beta)$ as described above in the context of FIGS. 9a, 10a and 10b. This storing process is represented in block 118 by the relationship $wn(\beta_{lap}, \beta_{full})$ to $w_n((\beta_{full}-\beta_{lap})+\beta_{lap}, n(\beta_{full}-\beta_{lap})+\beta_{full}))$.

After block 118, control again passes to block 110 where counter n is again incremented by 1. The process corresponding to blocks 110, 112, 114, 116 and 118 is repeated until all of the helical weighting functions corresponding to the optimal number of images zsn have been scaled and the scaled functions have been added. Thereafter, control passes to block 120 and then the algorithm ends at block 122.

It should be understood that the methods and apparatuses described above are only exemplary and do not limit the scope of the invention, and that various modifications could be made by those skilled in the art that would fall under the scope of the invention. For example, while the invention is described above as including identification of an optimal data range $\beta_z$ and an optimal number zns of images to be combined to generate a thick image as well as a process for reducing the time required to combine helical weighting functions, it should be appreciated that each of these three concepts is valuable in its own right. For instance, using the inventive process to determine optimal number zsn itself may be valuable in the context of other algorithms to add helical weights. As another instance, the weight adding process clearly is advantageous independent of the other concepts.

To apprise the public of the scope of this invention, the following claims are made:

1. A method to be used with a set of CT helical data corresponding to a thick slice of interest (TSOI), the method for generating a thick slice data weighting function w(β) by combining slice specific Z-smoothing scalars zw and helical slice image weight functions hw corresponding to first through N slice images to be combined to generate the thick slice image corresponding to the TSOI, the method comprising the steps of:

(a) for the first slice, mathematically combining the helical weight function hw and an image specific scalar zw(n) to generate a scaled weighting function $w_n(\beta)$ corresponding to the first slice;

(b) storing scaled weighting function $w_n(\beta)$ weights at the beginning of an intermediate weighting array $w_{int}(\beta)$;

(c) for the next adjacent slice, mathematically combining the helical weighting function hw and an image specific scalar zw(n) to generate a scaled weighting function $w_n(\beta)$;

(d) identifying an overlapping segment of the scaled weighting function $w_n(\beta)$ that overlaps an overlapped segment of the intermediate weighting array $w_{int}(\beta)$ and adding the overlapping segment weights to the overlapped segment weights;

(e) storing the function $w_n(\beta)$ segment weights that do not overlap the intermediate weighting function array at the end of the intermediate weighting function array;

(f) repeating steps (c) through (e) for each of the slice images to be combined to generate the thick image; and (g) outputting the intermediate weighting function array as a final weighting array $w_n(\beta)$.

2. The method of claim 1 wherein the steps of mathematically combining include the step of multiplying a scalar by a corresponding function.

3. The method of claim 1 also for use with a system wherein an optimal Z-smoothing factor zsf is provided and also for identifying an optimal number zns of two dimensional images corresponding to data to be combine to generate a thick image, the method further including the step of mathematically manipulating the zsf factor to identify the optimal value zns.

4. The method of claim 3 wherein the step of mathematically manipulating includes the step of solving the following equation:

$$zns=2fceil(zsf-1)+1$$

where fceil is a ceiling function that rounds decimal values up to the next integer value.

5. The method of claim 1 also for use with a system wherein an optimal Z-smoothing factor zsf is provided and also for identifying an optimal set of data to be used to generate the thick image, the method further comprising the step of solving the following equation to determine the optimal set of data $\beta_z$ as a function of gantry angle by solving the following equation:

$$\beta_z=\beta_n(zsf+1)$$

where $\beta_n$ is half of the minimum gantry rotation angle spanned by the center CT detector in any detector row required to collect data needed to generate a single slice image while $\beta_z$ is the gantry rotation angle spanned by the center detector of the same row required to collect data needed to generate a thick image according to a Z-smoothing algorithm.

6. The method of claim 5 further including the step of applying the final weighting array $w_n(\beta)$ to the data corresponding to gantry angle $\beta_z$.

7. A method to be used with a set of CT helical data corresponding to a thick slice of interest (TSOI), the method for generating a thick slice data weighting function $w(\beta)$ by combining Z-smoothing functions zw and helical slice image weight functions hw, the thick slice data weighting function useable to generate a thick slice image corresponding to the TSOI, the method comprising the steps of, where a slice image quantity is identified as N:

(a) setting a slice counter n to zero;

(b) mathematically combining hw and zw(n) to generate a scaled weighting function $w_n(\beta)$;

(c) storing function segment $w_n(\beta i, \beta_{full})$ to intermediate function segment $w(\beta i, \beta_{full})$;

(d) incrementing counter n;

(e) if n is equal to N, skipping to step (g), else:
   (1) mathematically combining hw and zw(n) to generate scaled weighting function $w_n(\beta)$;
   (2) adding $w_n(0,\beta_{lap})$ to $w_{iti}(n(\beta_{full}-\beta_{lap}), n(\beta_{full}-b_{lap})+\beta_{lap}))$;
   (3) storing $w_n(\beta_{lap}, \beta_{full})$ to $w_{iti}(n(\beta_{full}-\beta_{lap})+\beta_{lap}, n(\beta_{full}-b_{lap})+\beta_{full}))$;

(f) repeating steps (d) through (e); and (g) outputting intermediate function $w_{iti}(\beta)$ as a final function $w_{iti}(\beta)$;

where the first and second angles $\beta 1$ and $\beta 2$ in each function segment $w_n(\beta 1, \beta 2)$ and $w(\beta 1, \beta 2)$ correspond to a first gantry angle in the corresponding function segment and the length of the function segment, respectively, $\beta i$ corresponds to the first angle in a function, $\beta_{full}$ corresponds to the total length of a scaled function, and $\beta_{lap}$ corresponds to the segments of adjacent weighting functions that overlap.

8. The method of claim 7 wherein each function zw is a scalar and the steps of mathematically combining include the step of scaling helical weighting function by a corresponding scalar.

9. The method of claim 7 also for use with a system wherein an optimal Z-smoothing factor zsf is provided and also for identifying an optimal number zns of two dimensional images corresponding to data to be combine to generate a thick image, the method further including the step of mathematically manipulating the zsf to identify the optimal value zns.

10. The method of claim 9 wherein the step of mathematically manipulating includes the step of solving the following equation:

$$zns=2fceil(zsf-1)+1$$

where fceil is a ceiling function that rounds decimal values up to the next integer value.

11. The method of claim 7 also for use with a system wherein an optimal Z-smoothing factor zsf is provided and also for identifying an optimal set of data to be used to generate the thick image, the method further comprising the step of solving the following equation to determine the optimal set of data $\beta_z$ as a function of gantry angle by solving the following equation:

$$\beta_z=\beta_n(zsf+1)$$

where $\beta_n$ is half of the minimum gantry rotation angle spanned by the center CT detector in any detector row required to collect data needed to generate a single slice image while $\beta_z$ is the gantry rotation angle spanned by the center detector of the same row required to collect data needed to generate a thick image according to a Z-smoothing algorithm.

12. The method of claim 11 further including the step of applying the final weighting array $w_n(\beta)$ to the data corresponding to gantry angle $\beta_z$.

13. An apparatus to be used with a set of CT helical data corresponding to a thick slice of interest (TSOI), the apparatus for generating a thick slice data weighting function $w(\beta)$ by combining Z-smoothing functions zw and helical slice image weight functions hw, the thick slice data weighting function useable to generate a thick slice image corresponding to the TSOI, the apparatus comprising, where a slice image quantity is identified as N:

a processor running a pulse sequencing program to perform the steps of:

(a) setting a slice counter n to zero;

(b) mathematically combining hw and zw(n) to generate scaled weighting function $w_n(\beta)$;

(c) storing function segment $w_n(\beta i, \beta_{full})$ to intermediate function segment $w_{iti}(\beta i, \beta_{full})$;

(d) incrementing counter n;

(e) if n is equal to N, skipping to step (g), else:
   (1) mathematically combining hw and zw(n) to generate scaled weighting function $w_n(\beta)$;
   (2) adding $w_n(0,\beta_{lap})$ to $w(n(\beta_{full}-\beta_{lap}), n(\beta_{full}-b_{lap})+\beta_{lap}))$;
   (3) storing $w_n(\beta_{lap}, \beta_{full})$ to $w(n(\beta_{full}-\beta_{lap})+\beta_{lap}, n(\beta_{full}-b_{lap})+\beta_{full}))$;

(f) repeating steps (d) through (e); and (g) outputting intermediate function $w_{iti}(\beta)$ as final function $w_{ti}(\beta)$;

where the first and second angles $\beta 1$ and $\beta 2$ in each function segment $w_n(\beta 1, \beta 2)$ and $w(\beta 1, \beta 2)$ correspond to a first gantry angle in the corresponding function segment and the length of the function segment, respectively, $\beta i$ corresponds to the first angle in a function, $\beta_{full}$ corresponds to the total length of a scaled weighting function, and $\beta_{lap}$ corresponds to the segments of adjacent weighting functions that overlap.

14. The apparatus of claim 13 wherein each function zw is a scalar and the program causes the processor to mathematically combine by multiplying a scalar by a corresponding helical weighting function.

15. The apparatus of claim 13 also for use with a system wherein an optimal Z-smoothing factor zsf is provided and also for identifying an optimal number zns of two dimensional images corresponding to data to be combine to generate a thick image, the program further causing the processor to mathematically manipulating the zsf to identify an optimal value zns.

16. The apparatus of claim 15 wherein the program causes the processor to mathematically manipulate by solving the following equation:

$$zns = 2fceil(zsf-1)+1$$

where fceil is a ceiling function that rounds decimal values up to the next integer value.

17. The apparatus of claim 13 also for use with a system wherein an optimal Z-smoothing factor zsf is provided and also for identifying an optimal set of data to be used to generate the thick image, the program further causing the processor to solve the following equation to determine the optimal set of data $\beta_z$ as a function of gantry angle by solving the following equation:

$$\beta_z = \beta_n(zsf+1)$$

where $\beta_n$ is half of the minimum gantry rotation angle spanned by the center CT detector in any detector row required to collect data needed to generate a single slice image while $\beta_z$ is the gantry rotation angle spanned by the center detector of the same row required to collect data needed to generate a thick image according to a Z-smoothing algorithm.

18. The apparatus of claim 17 wherein the program further causes the processor to apply the final weighting array $w_{ti}(\beta)$ to the data corresponding to gantry angle $\beta_z$.

19. A method to be used with a set of CT helical data corresponding to a thick slice of interest (TSOI) and a CT system that provides an optimal Z-smoothing factor zsf, the method for identifying an optimal number zns of slice images through the TSOI to be combined to generate a thick image corresponding to the TSOI, the method comprising the step of solving the following equation:

$$zns = 2fceil(zsf-1)+1$$

where fceil is a ceiling function that rounds decimal values up to the next integer value.

20. An apparatus to be used with a set of CT helical data corresponding to a thick slice of interest (TSOI), the apparatus for generating a thick slice data weighting function $w(\beta)$ by combining slice specific Z-smoothing scalars zw and helical slice image weight functions hw corresponding to first through N slice images to be combined to generate the thick slice image corresponding to the TSOI, the apparatus comprising:

a processor running a pulse sequencing program to perform the steps of:

(a) for the first slice, mathematically combining the helical weight function hw and an image specific scalar zw(n) to generate a scaled weighting function $w_n(\beta)$ corresponding to the first slice;

(b) storing weighting function $w_n(\beta)$ weights at the beginning of an intermediate weighting array $w_{iti(\beta)}$;

(c) for the next adjacent slice, mathematically combining the helical weighting function hw and a slice specific scalar zw(n) to generate a scaled weighting function $w_n(\beta)$;

(d) identifying an overlapping segment of the scaled weighting function that overlaps an overlapped segment of the intermediate weighting array and adding the overlapping segment weights to the overlapped segment weights;

(e) storing the scaled function $w_n(\beta)$ segment weights that do not overlap the intermediate weighting function array at the end of the intermediate weighting function array;

(f) repeating steps (c) through (e) for each of the slice images to be combined to generate the thick image; and (g) outputting the intermediate function as a final weighting array $w_{ti}(\beta)$.

* * * * *